United States Patent [19]

Kleber et al.

[11] Patent Number: 4,992,595
[45] Date of Patent: Feb. 12, 1991

[54] POLY(ALKOXY ETHER) MIXED FORMALS

[75] Inventors: Rolf Kleber, Neu-Isenburg; Siegfried Billenstein, Burgkirchen; Lothar Jaeckel, Flörsheim am Main; Ignaz Wimmer, Winhöring, all of Fed. Rep. of Germany

[73] Assignee: Hoechst Aktiengesellschaft, Frankfurt, Fed. Rep. of Germany

[21] Appl. No.: 274,698

[22] Filed: Nov. 23, 1988

Related U.S. Application Data

[63] Continuation-in-part of Ser. No. 144,253, Jan. 14, 1988, abandoned.

[30] Foreign Application Priority Data

Jan. 17, 1987 [DE] Fed. Rep. of Germany ....... 3701303

[51] Int. Cl.$^5$ ............................................. C07C 43/30
[52] U.S. Cl. ................................................... 568/601
[58] Field of Search ........................................ 568/601

[56] References Cited

U.S. PATENT DOCUMENTS 4,294,990 10/1981 Kleber et al. .
4,364,770 12/1982 Grunert et al. ...................... 568/601

Primary Examiner—Howard T. Mars
Attorney, Agent, or Firm—Connolly and Hutz

[57] ABSTRACT

Compounds of the formula

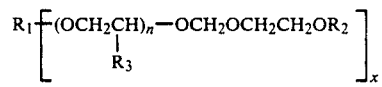

where $R_1$ denotes a group of the formula

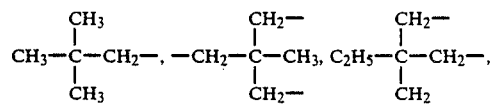

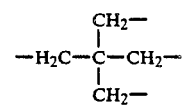

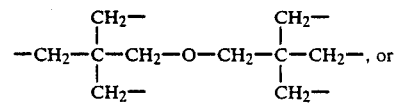

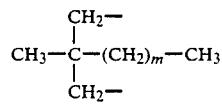

$R_2$ denotes $C_1$–$C_4$-alkyl, $R_3$ denotes hydrogen or methyl, n denotes a number from 5 to 100, m denotes an integer from 0 to 4 and x denotes the number of free valences of the particular $R_1$ radical, a process for the preparation thereof, and the use thereof as fiber spin finishes.

1 Claim, No Drawings

POLY(ALKOXY ETHER) MIXED FORMALS

This application is a continuation-in-part of application Ser. No. 07/144,253, filed 1/14/88, now abandoned.

DE-C No. 2,812,443 discloses polyglycol ether mixed formals of the formula $$R_1-(OC_2H_4)_n-OCH_2OCH_2CH_2OR_2$$

where $R_1$ denotes $C_8$–$C_{22}$-alkyl, $R_2$ denotes $C_1$–$C_4$-alkyl and n denotes numbers from 3 to 30. These compounds are employed as fiber spin finishes and have become firmly established in practice. With the growth of the friction texturing process on polyurethane (PUR) disks, it has become apparent, however, that the products claimed in DT-C No. 2,812,443 do not meet the demands of practice, in spite of the low swelling tendency for yarn. This is because these polyglycol ether mixed formals tend to swell the PUR friction disks, so that the disk lives in the friction texturing process are limited. It is therefore necessary to develop products which have the low filament/metal friction of known polyglycol ether mixed formals, but do not swell PUR friction disks in practical operation.

It has now been found that these conditions are met by formals which are derived from certain polyhydric alcohols.

The invention relates to compounds of the formula I $$R_1\left[(OCH_2CH)_n-OCH_2OCH_2CH_2OR_2\right]_x \quad (1)$$
$$\phantom{R_1[(OCH_2CH)_n}R_3$$

where $R_1$ denotes a group of the formulae

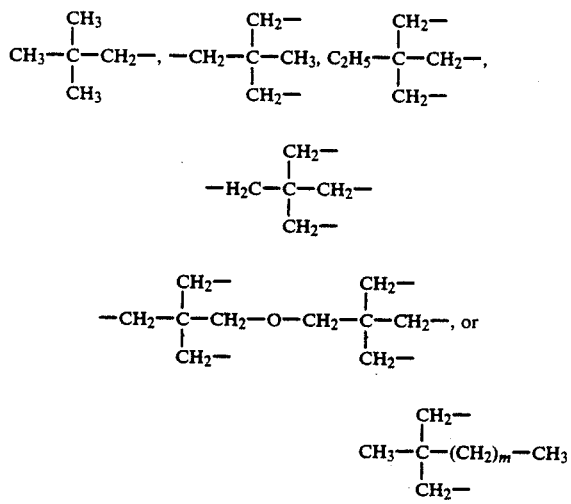

where $R_2$ denotes $C_1$–$C_4$-alkyl, $R_3$ denotes hydrogen or methyl, n denotes a number from 5 to 100, m denotes an integer from 0 to 4 and x denotes the number of free valences of the particular $R_1$ radical.

These compounds are prepared by the process described in DE-A No. 2,523,588, in which a compound of the formula (2)

$$R_1\left[(OCH_2CH)_2-OH\right]_x \quad (2)$$
$$\phantom{R_1[(OCH_2CH)_2}R_3$$

is reacted with a dialkylglycol normal of the formula (III)

$$CH_2(OC_2H_4OR_2)_2 \quad (3)$$

in the presence of a strong acid while simultaneously removing the glycol monoalkyl ether produced in this reaction. The compounds of the formula (II) are prepared by alkoxylation of the alcohols of the formula $R_1(OH)x$ using ethylene oxide and/or propylene oxide in a known fashion, either oxyethylates or oxypropylates or random or block copolymers being present. The molecular weight of the starting oxyalkylates is characterized by means of the viscosity at 50° C. Very favorable compounds have a viscosity of 50–1,000 mPa s at 50° C. Excessively high molecular weights lead to oiling-up of the PUR disks by the compounds according to the invention.

As a consequence of their unexpected low filament/metal friction, which is apparent as a high lubrication effect, the compounds of the above formula (I) are very high suitable as lubricants. In addition, these compounds, in contrast to the compounds known from DE-C No. 2,812,443, do not lead to swelling of the PUR disks during friction texturing.

These mixed formals are applied by conventional methods, for example by slop padding, dipping or spraying. During application, these compounds can be applied in pure form to the fibers or alternatively from dilute aqueous solution. Since the mixed formals are water-soluble, no additional emulsifiers are required here, in contrast to mineral and ester oils. These mixed formals can also be admixed with components which are conventional for fiber finishing, such as, for example, antistatic agents and cohesion promoters. Suitable types of fiber which can be finished using these mixed formals are all synthetic and natural fibers, such as, for example, polyester, polyacrylonitrile, polyamide or cellulose. The active substance coating of these mixed formals on the fibers is about 0.5 to 1.5 % by weight for warp and weaving finishes and about 0.1 to 1.0 % by weight for texturing finishes. They can also be employed as anhydrous formulations for spool oils or for final brightening after dyeing and after other processing processes. In this case, the active substance coating is about 1–5% by weight for spool oils and about 0.3–0.8% by weight for final brightening. Due to the instability in the acidic pH range, these finishes can easily be destroyed by slightly acidifying the waste water after washing out the finish. The decomposition products produced are readily biodegradable. In some cases, it is sufficient to pass air through the waste water in order to decompose the mixed formals.

The following mixed formals were prepared analogously to the process given in Example 1 of DE-C No. 2,812,443:

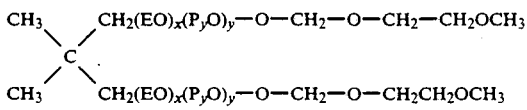

2,2-dimethylpropanediol-(EO/P$_y$0 mixed oxyalkylate)-methyl glycol mixed formal.

$x+y$ = random
ratio 4:1 parts by weight
initial viscosity: 50° C.: 200 mPa s

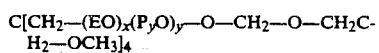 (b)

Pentaerythritol-(EO/P$_y$0 mixed oxyalkylate)-methyl glycol mixed formal $x+y$ = random
ration 4:1 parts by weight
initial viscosity of the oxyalkylate: 50° C.: 300 mPa s

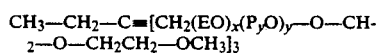 (c)

Trimethylolpropane-(EO/P$_y$0 mixed oxyalkylate)-methyl glycol mixed formal.

$x+y$ = random
ratio 1:4 parts by weight
initial viscosity of the oxyalkylate: 50° C. 100 mPa s.
For comparison, the compounds

| | | |
|---|---|---|
| (d) C$_{12/14}$(EO)$_5$—O—CH$_2$—O—CH$_2$CH$_2$—O—CH$_3$ | (DE-C 2,812,443) | |
| (e) C$_{12/14}$-(EO)$_5$—O—CH$_2$—O-n-C$_4$H$_9$ | (DE-A 2,523,588) | |
| (f) C$_{12/14}$(EO)$_5$—O—C$_4$H$_9$ | (US-A 3,997,450) | | were prepared.

PUR disks were placed in these products so that the disks were completely covered, and the products were warmed at 90° C. for 7 days in a sealed glass container.

After this time, the disks were assessed visually as follows:

| Product: | PUR disk |
|---|---|
| a: | unchanged |
| b: | unchanged |

-continued

| Product: | PUR disk |
|---|---|
| c: | unchanged |
| d: comparison | destroyed |
| e: comparison | destroyed |
| f: comparison | destroyed |

Similar effects were obtained for the compound

TME(EO)$_x$(P$_y$O)$_y$—O—CH$_2$—O—CH$_2$—CH$_2$—O—nC$_4$H$_9$ according to the invention.

$x+y$ = block
$x+y$ = 1:1
viscosity at 50° C.: 400 mPa s
TME = trimethylolethyl

We claim:

1. A polyglycol ether mixed formal of the formula

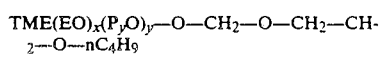

where R$_1$ denotes a group of the formula

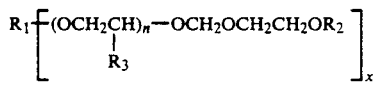

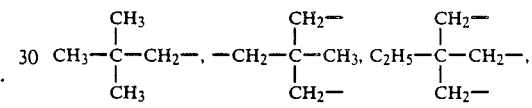

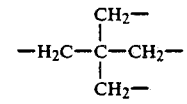

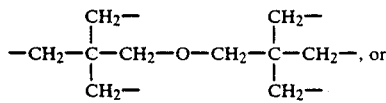

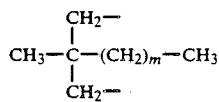

R$_2$ denotes C$_1$-C$_4$-alkyl, R$_3$ denotes hydrogen or methyl, n denotes a number from 5 to 100, m denotes an integer from 0 to 4 and x denotes the number of free valences of the particular R$_1$ radical.

* * * * *